(12) United States Patent  
Murata

(10) Patent No.: US 6,617,486 B1
(45) Date of Patent: Sep. 9, 2003

(54) FIRST AID ADHESIVE PLASTER

(75) Inventor: Takaaki Murata, Kumamoto-ken (JP)

(73) Assignee: Aso Seiyaku Kabushiki, Kumamoto-ken (JP)

( * ) Notice: Subject to any disclaimer, the term of this patent is extended or adjusted under 35 U.S.C. 154(b) by 0 days.

(21) Appl. No.: 09/534,981

(22) Filed: Mar. 27, 2000

(30) Foreign Application Priority Data

Mar. 27, 1999 (JP) ............................................. 11-124708
Oct. 9, 1999 (JP) ............................................. 11-324499

(51) Int. Cl.⁷ ................................................ A61F 13/00
(52) U.S. Cl. ........................... 602/48; 602/42; 602/54; 604/304; 604/306; 604/307; 424/447; 424/448
(58) Field of Search ................................ 424/443, 444, 424/445, 446, 447, 448, 449; 602/41–59; 604/304, 305, 306, 307; 128/888, 889

(56) References Cited

U.S. PATENT DOCUMENTS 4,808,172 A * 2/1989 Murata ........................ 604/306
6,120,792 A * 9/2000 Juni ............................. 424/448

* cited by examiner

Primary Examiner—Kim M. Lewis
(74) Attorney, Agent, or Firm—Ronald E. Greigg

(57) ABSTRACT

A first aid adhesive plaster comprising a pad on an upper surface of which an ointment is laid, an adhesive sheet of rectangular and an ointment protect cover formed to be a blister having a dome section by making its central portion project upwardly to form a gentle arc. The pad is covered with the blister by applying the ointment protect cover onto the adhesive sheet separably while leaving a gap between the ointment on the pad and an undersurface of the blister.

3 Claims, 7 Drawing Sheets

FIRST AID ADHESIVE PLASTER

BACKGROUND OF THE INVENTION

1. Field of the Invention

This invention relates to a first aid adhesive plaster for healing a wound by applying a pad with a layer of an ointment onto an affected part of skin such as an incised wound.

2. Prior Art

Various types of the first aid adhesive plaster have been on market for sale. For example, a plaster is well known in which a pad of gauze, impregnated with a liquid medicament for treating an infection or for healing a wound and then dried, is adhered onto a middle part of an upper surface of an adhesive sheet, and the upper surface of the pad is covered with a release sheet which is separable in the right and left directions. However, in such an adhesive plaster with the above-mentioned composition, since the liquid medicament is dry, there is a fear that the affected part of skin such as a wound ("a wound" hereinafter) may be hurt, and further effective sterilizing and healing effects cannot be obtained even if the pad is applied onto the wound, unless the dried liquid medicine is dissolved and exuded by a secretion from the wound.

In view of the above circumstances, a first aid adhesive plaster has been developed in which a capsule occluding a liquid medicament is laid over an upper surface of a pad without impregnating the pad with the liquid medicament nor being hardened. When the first aid adhesive plaster is used, by pressing the upper surface of the capsule ruptures a film of aluminum foil which forms a bottom of the capsule, so that the liquid medicine occluded in the capsule may be flown out and impregnated in the pad.

However, in the first aid adhesive plaster as above-mentioned, since a liquid medicament has to be occluded in the capsule, it only requires considerable manufacturing processes and wherefore high manufacturing cost, but also requires to rupture the film when the first aid adhesive plaster is used as above-mentioned. Therefore, it may sometimes happen that the liquid medicament splashes and cannot accurately be impregnated in the pad. Further, in case the film is ruptured when the pad is in a slanting position, there is a fear that a part of the liquid medicament remaining therein, and as a result, a volume of the medicament to work on the wound is reduced whereby healing effect weakened. Still further, because the liquid medicament with high fluidity is applied to all of the above-mentioned first aid adhesive plasters, the surface of the pad directly touches the wound, and therefore removal of the pad from the wound causes a pain, and the wound reopens. As a result, complete recovery is delayed.

In view of the above-mentioned circumstances, a first aid adhesive plaster with a pad applied with an ointment instead of liquid medicament is required. However, in case the pad applied with a layer of the ointment is covered with a release paper, there is a fear that the ointment is dried in a short period of time or the effect of the ointment is considerably weakened due to a change of quality by an influence of air coming from a gap between the adhesive sheet and the release paper. Further, even if the ointment is completely sealed up, when external pressure is given to the surface of the release paper while the first aid adhesive plaster is being carried or when the same is being used, there may be the cases that the ointment is squeezed out of the pad and becomes unable to be used. In addition, when the release paper is removed, a part of the ointment is transferred to the back of the release paper, and a volume of the ointment to work on the wound is reduced just like the above-mentioned liquid medicament which is occluded in a capsule.

In case the ointment is occluded in the above-mentioned capsule in order to solve such problems like the change in quality and the squeeze and crush of the ointment by unexpected external pressure, there is a problem that it is difficult to transfer a large volume of the ointment onto the pad even if the capsule is pressed to be deformed by which pressure the film of an aluminum foil forming the bottom of the capsule is raptured, as the ointment is already adhered to the inner surface of the capsule.

SUMMARY OF THE INVENTION

In view of the above-mentioned circumstances, this invention has an object to provide a first aid adhesive plaster in which an ointment stuck or applied onto a pad can be sealed up without causing a change in the quality of the ointment for a long period of time and hardly be squeezed and deformed even by external pressure, but it is easy to use just like the conventional first aid adhesive plasters with a simple composition.

To achieve the above object, a first aid adhesive plaster of the present invention comprises a pad on an upper surface of which an ointment is laid, an adhesive sheet of rectangular shape; said pad being applied in a central portion of an upper surface of the adhesive sheet, and an ointment protect cover formed to be a blister having a dome section by making its central portion project upwardly to form a gentle arc, wherein the pad is covered with the blister by applying the ointment protect cover onto the adhesive sheet separably while leaving a gap between the ointment on the pad and an undersurface of the blister.

The first aid adhesive plaster is characterized in that the blister is formed to be rectangular shape in plan view and provides both long side walls which are formed to be standing walls and inclined from their lower ends to approach each other upwardly.

In one embodiment the present invention relates to a first aid adhesive plaster which provides an ointment protect cover having another structure of a blister. Namely, the first aid adhesive plaster comprises a pad on an upper surface of which an ointment is laid, an adhesive sheet of rectangular; said pad being applied in a central portion of an upper surface of the adhesive sheet, and an ointment protect cover formed to be a blister having a rectangular form in plan view by making four walls thereof higher than the height of a width of the pad having the ointment, and also by making its central portion of the ointment protect cover project, wherein the pad is covered with the blister by applying the ointment protect cover onto the adhesive sheet separably.

In another embodiment of the present invention, the first aid adhesive plaster comprises a projection which is formed with a ceiling wall of the blister to project upwardly and to be made in parallel with a longitudinal direction of the blister.

In still another embodiment the present invention is characterized in that the undersurface of a ceiling wall of the blister provides a projection for preventing the blister from deforming downwardly by contacting the lower end of the projection with the pad.

In yet another embodiment the present invention further comprises a guard film applied onto the undersurface of the pad, said guard film being made to prevent permeation of the composition of the adhesive agent of the adhesive sheet, and a net covering from the upper surface of the pad to the undersurface of the guard film, both sides of said net being fixed to the both sides of the pad integrally by means of hot melt, wherein the ointment is applied from the upper surface of the net onto the pad through the mesh of the net so as to support the ointment by means of the mesh of the net.

In still a further embodiment of the invention the the pad comprises at least two layers. In still another embodiment the invention further comprises a separable paper interposed between both ends of the ointment protect cover in its longitudinal direction and both ends of the adhesive sheet in its longitudinal direction.

Functions and Advantages:

Since the ointment on the pad is covered with the blister of the ointment protect cover and the ointment protect cover is applied onto the adhesive layer of the adhesive sheet entirely, including the periphery of the opening lower end of the blister, the ointment applied onto the pad is sealed in the blister in such a state that the pad is isolated from the open air, and therefore there is no fear that the ointment changes in quality or becomes hardened.

Further, since the blister is formed to be a dome in section by making its central portion project upwardly to form a gentle arc, where pressure acts on the upper surface of the blister at the time of using or carrying the same, it becomes possible to surely prevent the blister from bending downwardly to curve. As a result, there is no fear that the ointment on the pad is pressed and flattened, and it becomes possible to prevent the ointment from trasnferring to the undersurface of the blister, so that almost all of the ointment on the pad may be applied onto a wound for cure.

Since both long side walls of the blister, which is formed in a rectangular in plan view, provides both long side walls which are formed to be standing walls and inclined from their lower ends to approach each other upwardly, strength of the blister against deformation due to compression may be further increased by means of the standing walls against the pressure acting on the tipper surface of the blister, so that it becomes possible to surely prevent the ointment from applying to the undersurface of the blister.

Since the blister formed in a central portion of the ointment protect cover, is made such that the four walls of the blister are higher than the height of a width of the pad having the ointment where a pressure acts on the upper surface of the blister, it becomes possible to support the pressure by means of the four walls which have the height higher than the width of the pad. Therefore, it may prevent the ceiling of the blister from deforming downwardly due to the pressure. In this case, since the projection is formed with a ceiling wall of the blister to project upwardly and to be made in parallel with a longitudinal direction of the blister, it also becomes possible to surely prevent the ceiling of the blister from bending and curving downwardly in combination with the four walls and the projection, so that it may eliminate such a state that a part of the ointment is adhered to the undersurface of the ceiling of the blister as the undersurface of the blister contacts with the ointment on the pad.

On the other hand, since the undersurface of a ceiling wall of the blister provides a projection for preventing the blister from deforming downwardly by contacting the lower end of the projection with the pad, when the blister is pressed unexpectedly with external forces at the time of using or carrying the same, it may prevent the blister from deforming and curving downwardly as the projection is received on the pad. As a result, it is no fear that the ointment on the pad is pressed and crushed, or that the ointment is adhered to the undersurface of the blister so that almost of the ointment on the pad may be supplied to a wound for cure.

Further, since the present invention uses such a simple structure that the ointment protect cover is adhered separably onto the uppersurface of the adhesive sheet and the pad is covered with the blister of the ointment protect cover, it becomes easy to manufacture the adhesive plaster and it is suitable for mass production to supply the same with a low price. And, since the ointment protect cover functions as a separable sheet, it becomes easy to use the adhesive plaster by exposing the pad having the ointment layer with a one-touch operation.

Furthermore, even if whole of the adhesive plaster is inclined or faced downward, it becomes possible to use the adhesive plaster by separating the ointment protect cover in the best posture for easily separate the same, and then immediately put the ointment of the pad onto the wound for covering the wound, since the ointment is always adhered onto the pad as a layer contrary to a medical fluid. At the time, the pad is not contacted with the wound directly contrary to a medical fluid which is impregnated in the pad, and therefore the wound is covered with the adhesive plaster softly so as to give an impression of good feeling of application.

Further, it becomes possible to easily separate the adhesive plaster without causing a pain or injuring the wound again when peeling off the adhesive plaster after cure. Still further, since the separable paper is interposed between both ends of the ointment protect cover and both ends of the adhesive sheet, it becomes possible to easily expose the pad having the ointment by separating or peeling off the ointment protect cover in such a manner that the end of the ointment protect cover is picked up.

Furthermore, it becomes possible to surely prevent chemical reaction of the ointment with the composition of the adhesive agent of the adhesive sheet since the guard film is applied onto the undersurface of the pad and the guard film is provides so called a gas-barrier function that may prevent permeation of the composition of the adhesive agent of the adhesive sheet, so that the effect of the ointment may be maintained for a long time.

Further, since the net is covered from the upper surface of the pad to the undersurface of the guard film, the ointment is supported by the mesh of the net in a state that the ointment is exposed upwardly of the mesh of the net and therefore it may prevent the ointment from moving outwardly and protruding from the pad, so that it may surely keep the predetermined applied state of the ointment. And, when using the same, by means of the net, it may prevent the pad from touching the wound directly so that it may peel off the adhesive plaster without injuring the wound again after use.

Still further, since the both sides of the net covering the pad are fixed to the both sides of the pad integrally by means of hot-melt, it does not cause that the net, the pad and the guard film are separated, and they may keep their states that they are always multiplied integrally each other in a center portion of the adhesive sheet. And, when manufacturing the adhesive plaster, it may deal with the net, the pad and the guard film integrally so as to carry out manufacturing of the first aid adhesive plaster efficiently.

Since the pad can be composed of more than two layers, even if the ointment of the uppermost layer on the pad is impregnated into the pad, it may prevent the ointment from impregnating into the pad on the lower side, so that the ointment may be used effectively for the wound.

Other advantages of the present invention will be apparent from the description of the embodiments with reference to the drawings.

BRIEF DESCRIPTION OF THE DRAWINGS

The drawings show embodiments of a first aid adhesive plaster according to this invention.

DETAILED DESCRIPTION OF THE PREFERRED EMBODIMENTS

Figure 1:
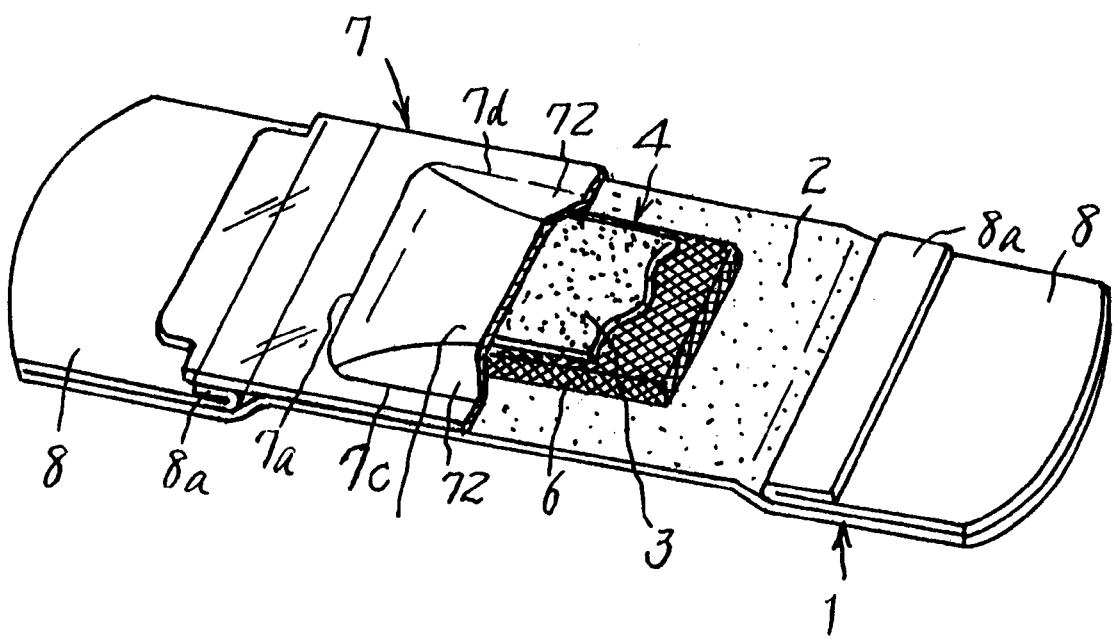
FIG. 1 is a perspective view of the first aid adhesive plaster partially taken away.
Figure 2:
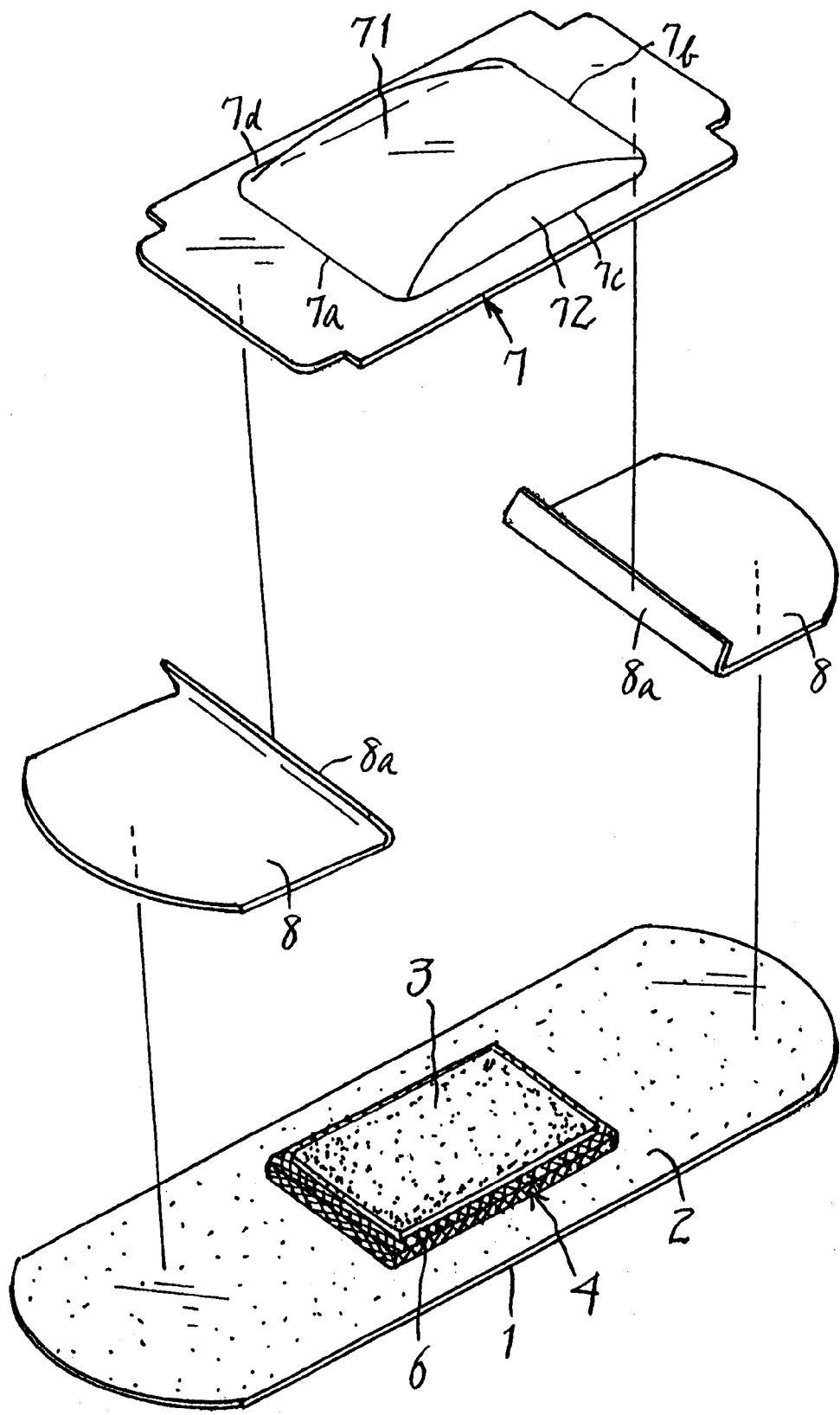
FIG. 2 is a perspective view of the adhesive plaster disassembled.
Figure 3:
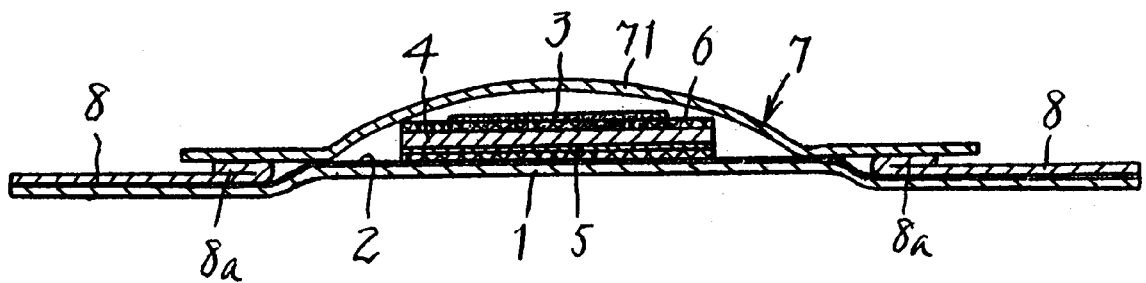
FIG. 3 is a sectional side view of the adhesive plaster.

Now, practical examples of this invention will be described with reference to the drawings. In FIGS. 1 through 3, an adhesive sheet 1 as a base of a first aid adhesive plaster is structured such than an adhesive agent layer 2 is applied onto whole of the uppersurface of a rectangular sheet having a predetermined width and length which is made of a thin plastic sheet, nonwoven fabric, woven fabric, papers or the like which has flexibility. The adhesive agent layer 2 is formed in a manner that an uppersurface of the above mentioned sheet is coated with an adhesive agent. Further, a pad 4 is arranged in a central portion of the uppersurface of the adhesive sheet 1, and the pad is provided with an ointment 3 on the uppersurface thereof and the undersurface of the pad 4 being applied to the adhesive agent layer 2.

Figure 4:
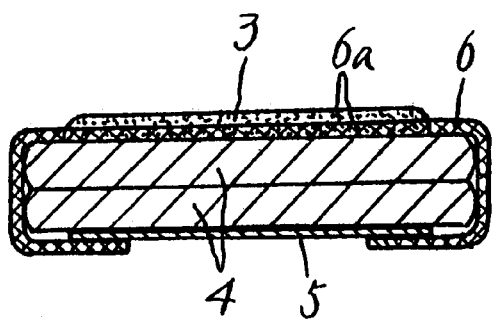
FIG. 4 is an enlarged sectional front view of a pad.
Figure 5A:
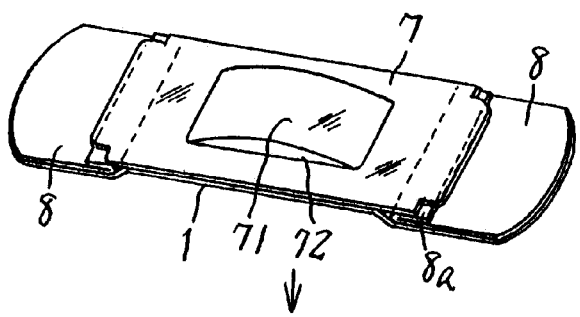
FIG. 5(a) through FIG. 5(d) are perspective views showing a manner of use.
Figure 5B:
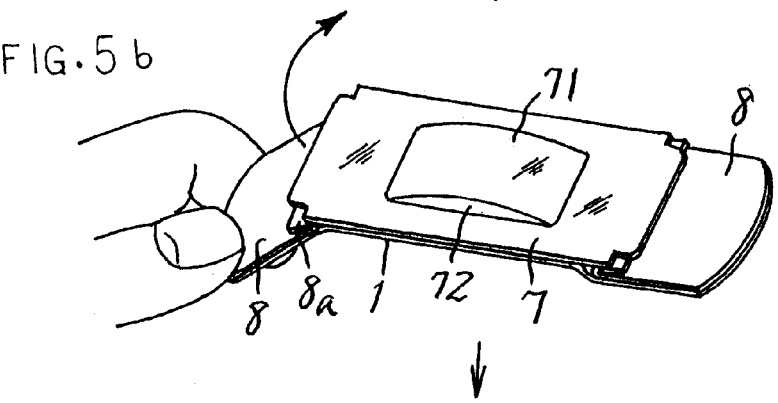
Figure 5C:
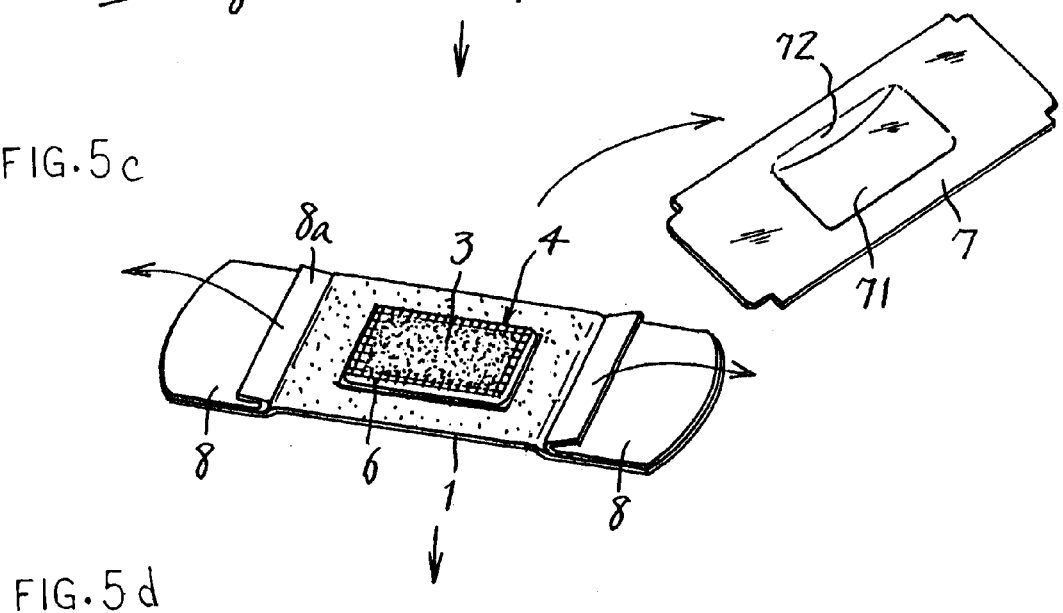
Figure 5D:
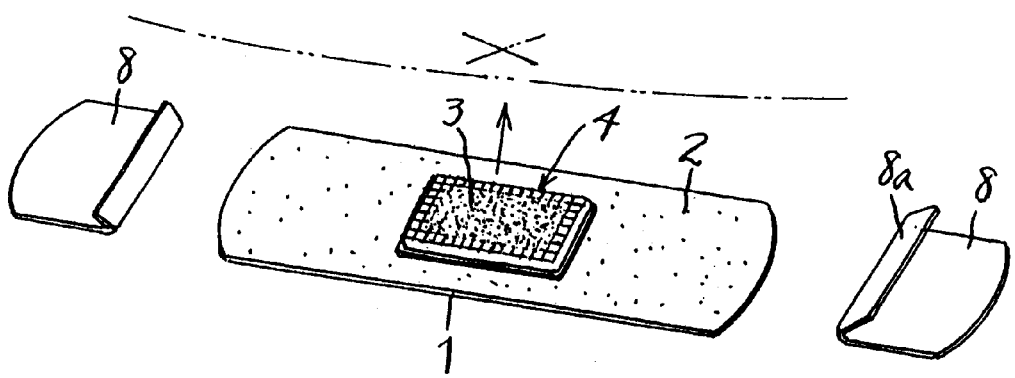

The pad 4 is made of a rectangular cloth such as a gauze which is disinfected, and its width is formed to be narrower than the width of the adhesive sheet I and its length is shorter than that of the adhesive sheet 1. Further, as shown in FIGS. 3 and 4, a thin guard film 5 having function of gas-barrier is multiplied onto the undersurface of the pad 4, and the guard film has the same form in plan view as that of the pad 4. A net 6 is arranged to cover from whole of the uppersurface of the pad 4 to the undersurface of the both sides of the guard film 5, and then the both sides of the net 6 are fixed to the both sides of the pad 4 integrally by means of hot-melt. A predetermined amount of the ointment 3 is applied onto the uppersurface of the pad thinly through a mesh 6a of the net 6. Accordingly, the ointment 3 becomes in a state that the ointment is supported by the mesh of the net 6, and therefore there is no fear that the ointment moves or flows laterally on the pad 4.

By the way, it is of course possible to make the pad with a single material, but it is preferable to compose the pad by multiplying more than two or three layers. With this structure, it becomes difficult to impregnate the ointment 3 into the pad as a lower layer due to the interface between the pad as the lower layer and its upper layer even if the composition of the ointment 3 is impregnated in the pad 4 with a capillary phenomenon, so that it may prevent the ointment 3 from deteriorating or hardening for a long period of time. Further, since the pad 4 is adhered to the adhesive agent layer 2 of the adhesive sheet 1 via the guard film 5 which is applied to the undersurface of the pad 4, it may prevent the composition of the adhesive agent of the adhesive sheet 1 from impregnating into the pad 4 by means of the guard film 5, so that it may surely prevent the ointment on the pad 4 from reacting chemically or deteriorating, and therefore, the effect of the ointment may be maintained for a long time. Furthermore, the ointment protect cover 7 is overlapped on the adhesive sheet 1, and the undersurface of the ointment protect cover 7 is applied separably to the adhesive agent layer 2. This ointment protect cover 7 is made of transparent plastics such as vinyl choloride having rigidity but non air-permeability, and formed to have the same width as the adhesive sheet 1 and provide a rectangular shape which is shorter than the length of the adhesive sheet 1. Furthermore, the ointment protect cover 7 is formed to upwardly 25 project its central portion in the longitudinal direction with a predetermined width and a predetermined length to make a gentle arc, so as to form a blister 71 which is in a shape of a dome opening its lower end wholly.

Describing the shape of the blister 71 in detail, at the four sides of the opening of the blister 71, which is formed to be a rectangular in plan view, the length of each of short sides 7a and 7b, which are in parallel with one another in the direction of the width of the ointment protect cover 7, and the length of each of long sides 7c and 7d, which are connected to the both ends of the short sides 7a and 7b, are made slightly longer than the length of each of the short side and the long side of the pad 4, so as to form an opening portion 72 having a space which is capable of receiving the pad 4. Further, by projecting the central portion of the ointment protect cover 7 upwardly from the short sides 7a and 7b to make a gentle arc so as to form a dome in section. Furthermore, in the long sides 7c and 7d at the opening lower end of the blister 71, the both sidewalls of the long sides are formed to be standing walls 72 and 72 of crescent in a side view, which are inclined upwardly in the direction that the standing walls are approaching each other.

The ointment protect cover 7 having the blister 71, which is formed as mentioned above, covers the pad 4, which is applied to the central portion of the uppersurface of the adhesive sheet 1, by means of the blister 71, and the undersurface of the ointment protect cover 7 including the undersurface of the periphery of the opening of the blister 71 is applied separably to the adhesive agent layer 2 of the adhesive sheet 1, except the undersurface of the both ends of the ointment protect cover 7 in the longitudinal direction, in such a state that the pad is received in the blister. The height of the ceiling of the blister 71 is formed to be slightly larger than the thickness of the pad 4 which provides the ointment 3 as a layer, and therefore, there is formed a clearance between the adhesive agent layer 2 on the pad 4 which is received in the opening end of the blister 71, and the undersurface of the ceiling of the blister 71, so that the adhesive agent layer 2 is not adhered to the undersurface of the ceiling of the blister 71.

Separable papers 8 are applied separably to the adhesive agent layer 2 on the both sides of the adhesive sheet 1 which project from the both ends of the ointment protect cover 7, and the inner ends of the separable paper 8 extend to the undersurface of the both ends of the ointment protect cover 7, so as to form overlapping ends 8a and 8a' by turning the extended portions upwardly, and then the both ends of ointment protect cover 7 are placed on the overlapping ends 8a and 8a'.

Since the first aid adhesive plaster as mentioned above, is in a state prior to use that the undersurface of the periphery of the blister 71 of the ointment protect cover 7 which covers the pad 4, is applied to the adhesive sheet 1, air does not go into the blister 71, and since the blister 71 has a shape of dome in section, even if a pressure acts on the uppersurface of the blister when carrying the adhesive plaster, it becomes possible to generate a strong resistant force against the pressure, and therefore it is no fear that the blister 71 may easily be deformed downwardly. Furthermore, since the both sides of the blister 71 are formed to be the standing walls 72 and 72 which form a crescent in a side view, so as to be inclined upwardly in the direction that the standing walls are approaching each other, it may also generate a strong resistance against the pressure so that it may prevent the adhesive agent layer 2 of the pad 4 from adhering to the undersurface of the blister 71.

Next, as shown in FIG. 5, when using the adhesive plaster, first, the ointment protect cover 7 is separated or peeled off from the adhesive sheet 1. At the time, the both ends of the ointment protect cover 7 are not adhered to the adhesive sheet 1, and since the separable papers 8 are interposed between the both ends of the ointment protect cover and the both ends of the adhesive sheet 1, picking the end of the adhesive sheet 1 by the fingers of one hand and also picking the end of the ointment protect cover 7 by the fingers of the other hand so as to move these away each other, so that the ointment protect cover 7 may be peeled off from the adhesive sheet 1 with so called one touch-action, as shown in FIGS. 5(b) and 5(c). Thus, it becomes possible to expose the pad 4 which is covered with the blister 71. Next, removing the separable papers 8 away from the both ends of the adhesive sheet 1, and then the pad 4 may fit a wound in such a manner that the ointment 5 on the pad 4 is pushed onto the wound and the adhesive sheet 1 is adhered to the skin.

Figure 6:
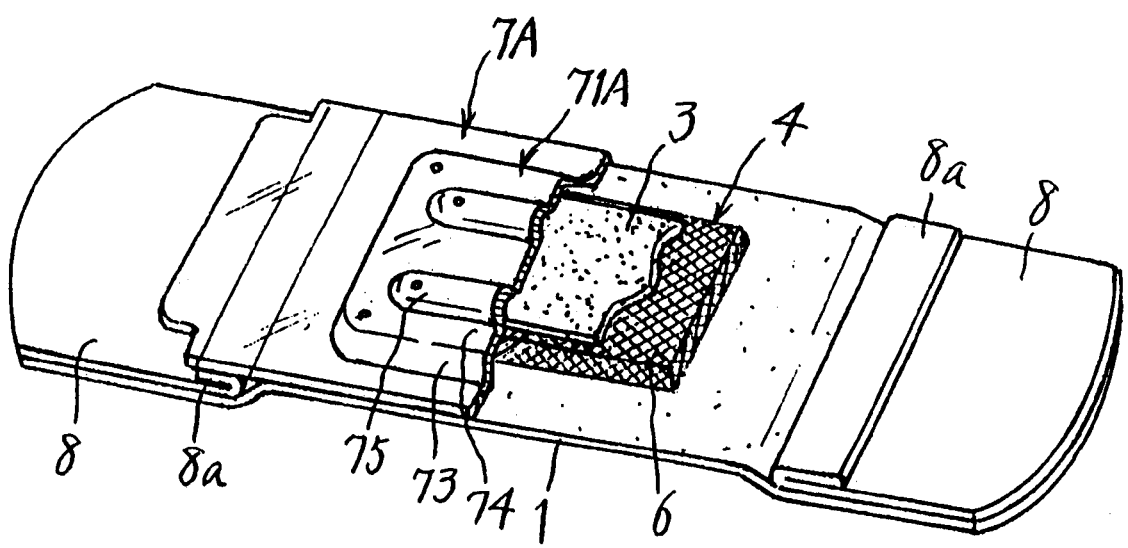
FIG. 6 is a perspective view of another first aid adhesive plaster partially taken away, according to this invention.
Figure 7:
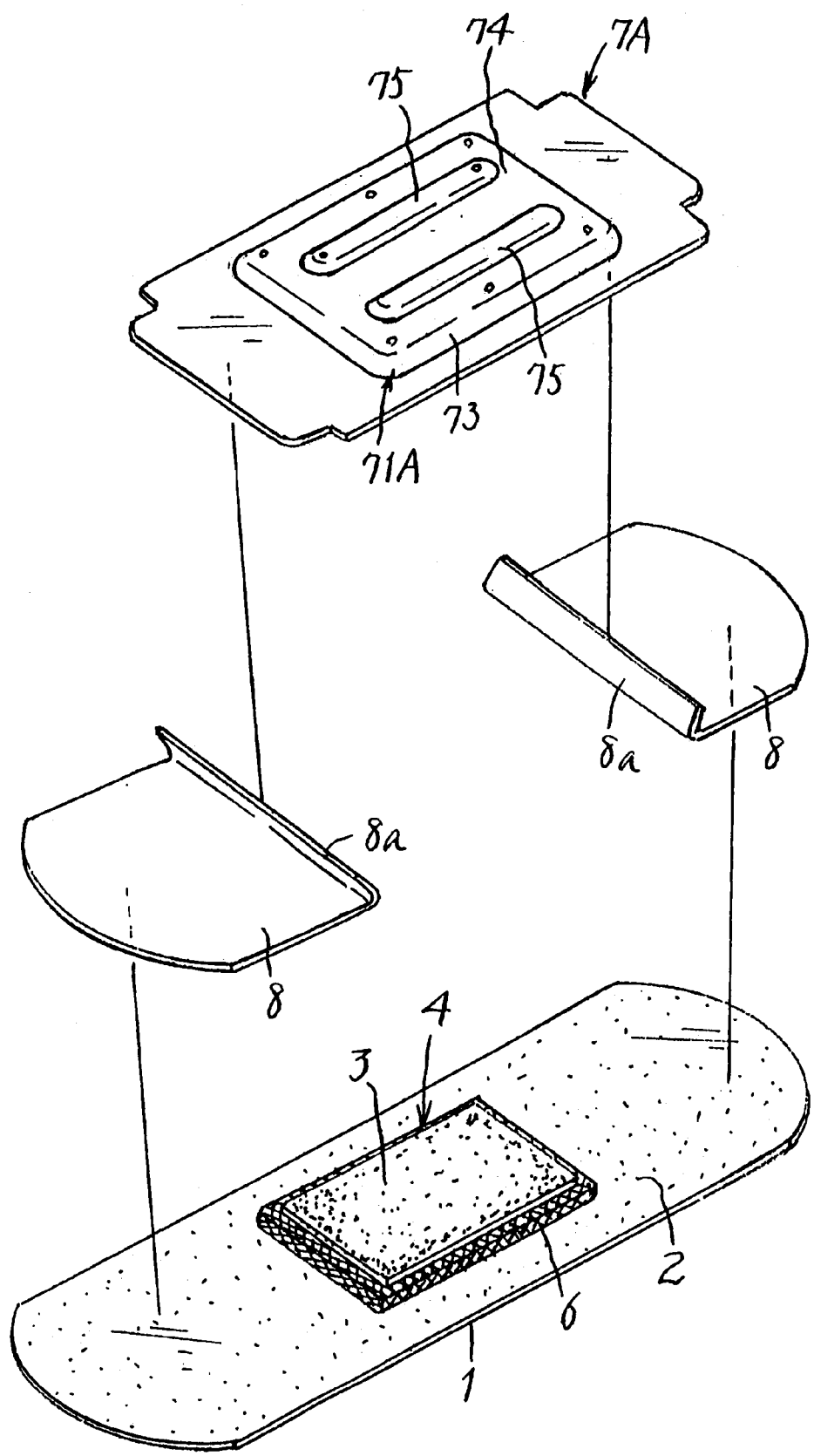
FIG. 7 is a perspective view of the adhesive plaster 15 disassembled.

FIGS. 6 and 7 show another embodiment of this invention, in which a first aid adhesive plaster is shown using a blister which is formed in another form. This blister 71A is the same as the above mentioned embodiment in such a structure that a predetermined width and a predetermined length of the central portion in the longitudinal direction of an ointment protect cover 74 of rectangular form are made to project upwardly so as to form the lower ends thereof to have an opening of rectangular form which may receive the pad 4. But, the blister 71A is made to project for forming a four directional peripheral wall 73, which has a height greater than the thickness of the pad 4 having the adhesive agent layer 2, in integral with a ceiling wall 74 which is in parallel with the upper end of the four directional peripheral wall 73, and therefore this blister is not made to project in the longitudinal direction to form a dome in section, as the fore-mentioned embodiment.

Namely, the blister 71A comprises the four directional peripheral wall 73 and the flat ceiling wall 74 and the lower end of the blister is formed to be a rectangular in plan view opening the lower end entirely. The height of the four directional peripheral wall 73 is formed greater than the thickness of the pad 4 (the thickness between the undersurface of the pad 4 and the uppersurface of the ointment 3), and the area surrounded by the inner periphery of the four directional peripheral wall 73 is formed to be a size larger than the area of the pad 4, so that the pad 4 having the ointment 3 may be received in the blister. Further, on the ceiling 74 of the blister 714, two line projections 75 and 75 are made to project upwardly in parallel with each other in the longitudinal direction thereof. The other structure of the first aid adhesive plaster having the above mentioned ointment protect cover 7A, is the same as the first embodiment and therefore its detailed description is omitted here by applying the same signs to the same parts.

As mentioned in the above embodiment, the ointment protect cover 7 covers the pad 4, which is applied to the central portion of the uppersurface of the adhesive sheet 1 of rectangular form by means of the blister 714, and the undersurface of the ointment protect cover 7 including the undersurface of the periphery of opening of the blister 71 is applied separably to the adhesive agent layer 2 of the adhesive sheet 1, except the undersurface of the both ends of the ointment protect cover 7 in the longitudinal direction, in such a state that the pad is received in the blister 71A. The height of the ceiling 74 of the blister 714 is formed to be slightly larger than the thickness of the pad 4 which provides the ointment 3 as a layer, and therefore, there is formed a clearance between the adhesive agent layer 2 on the pad 4 which is received in the opening end of the blister 714, and the undersurface of the ceiling of the blister 714, so that the adhesive agent layer 2 is not adhered to the undersurface of the ceiling 74 of the blister 714.

Further, separable papers 8 and 8 are applied separably to the adhesive agent layer 2 on the both sides of the adhesive sheet 1 which project from the both ends of the ointment protect cover 74, and the inner ends of the separable paper 8 extend to the undersurface of the both ends of the ointment protect cover 74, so as to form overlapping ends 8a and 8a by turning the extended portions thereof upwardly, and then the both ends of the ointment protect cover 74 are placed on the overlapping ends 8a and 8a.

Since the first aid adhesive plaster as mentioned above, is in a state prior to use that the undersurface of the periphery of the blister 71 of the ointment protect cover 7 which covers the pad 4, is applied to the adhesive sheet 1, air does not go into the blister 71. Further, since the line projections 75, which are in parallel with each other in the longitudinal directions of the blister 714, are made to project upwardly from the ceiling 74 of the blister 714, even if a pressure acts on the uppersurface of the blister 714 when carrying the adhesive plaster, it may strongly prevent the blister from deforming downwardly by means of the line projections and also the four directional peripheral wall 73 may prevent whole of the blister from compressing and deforming downwardly. As a result, it may avoid such a situation that the undersurface of the blister 74 may contact the ointment 3 on the pad 4 and a part of the ointment 3 is adhered to the undersurface of the ceiling of the blister 74. By the way, the manner of use of the adhesive plaster is the same as the above mentioned embodiment and therefore its description is omitted here.

Figure 8:
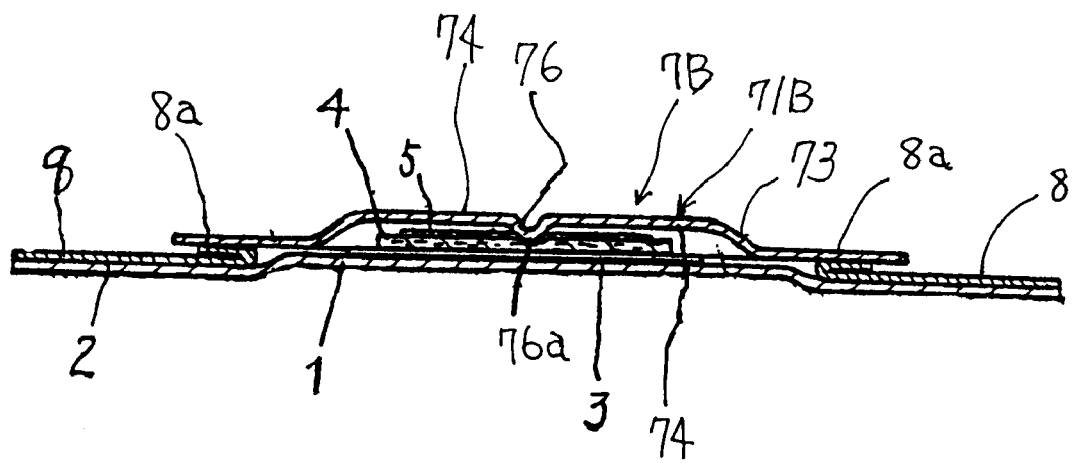
FIG. 8 is a sectional side view of another first aid adhesive plaster according to this invention.
Figure 9:
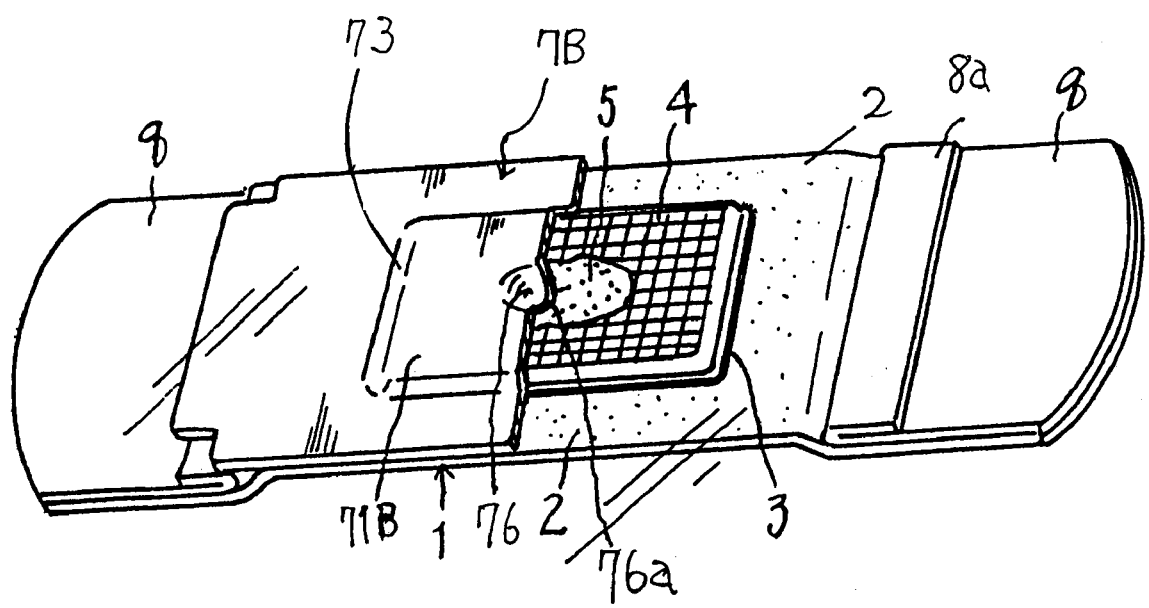
FIG. 9 is a perspective view of the adhesive plaster partially taken away.

FIGS. 8 and 9 show another embodiment of this invention and in the first aid adhesive plaster of FIGS. 6 and 7, instead of the line projections 75, which is provided with the ceiling 74 of the blister 714, the structure of this embodiment is characterized in that a projection 76 is made to project downwardly from the undersurface of a ceiling wall blister 74 of the blister 71B for preventing the blister 71B from deforming downwardly due to contact of the lower end of the blister with the pad 4.

Namely, the first aid adhesive plaster of this embodiment is the same as the first aid adhesive plaster as shown in FIGS. 6 and 7 in such points that the blister 71B comprises four directional peripheral wall 73 and a flat ceiling wall 74 and the lower end of the blister is formed to be a rectangular in plan view opening the lower end entirely, and that the height of the four directional peripheral wall 73 is formed greater than the thickness of the pad 4, and the area surrounded by the inner periphery of the four directional peripheral wall 73 is formed to be a size larger than the area of the pad 4, so that the interior of the blister 71B may be formed to have a space for receiving the pad 4 having the ointment 3 thereon. However, in this embodiment, in the central portion of the undersurface of the ceiling wall 74 of the blister 71B, a projection 76 is made to project downwardly so as to contact the lower end thereof with the pad 4.

This projection 76 is made to have a projecting lower end surface which forms a projecting arc surface or a flat surface 76a, and the projecting lower end surface 76a is contacted with and received by the uppersurface of the pad 4, and therefore even if a pressure acts on the blister in the downward direction, the ceiling wall 74 may prevent the blister from deforming downwardly, so that it may prevent the ointment 3 from adhering to the lower undersurface of the ceiling 74 by always keeping a small clearance between the ointment 3 on the pad and the ceiling wall 74. By the way, it is not limited that the projection 76 is single, but it may provide two or three projections 74 with the undersurface of the ceiling wall 74.

As mentioned in the above embodiment, the ointment protect cover 7B covers the pad 4, which is applied to the central portion of the uppersurface of the adhesive sheet 1 of rectangular form by means of the blister 71B, and the undersurface of the ointment protect cover 7B including the undersurface of the periphery of the opening of the blister 71B is applied separately to the adhesive agent layer 2 of the adhesive sheet 1, except the undersurface of the both ends of the ointment protect cover 713 in the longitudinal direction, in such a state that the pad is received in the blister 71B. The height of the ceiling 74 of the blister 71B is formed to be slightly larger than the thickness of the pad 4 which provides the ointment 3 as a layer, and therefore, there is formed a clearance between the adhesive agent layer 2 on the pad 4 which is received in the opening end of the blister 71B, and the undersurface of the ceiling of the blister 71B, so that the adhesive agent layer 2 is not adhered to the undersurface of the ceiling 74 of the blister 71B.

Further, separable papers 8 are applied separably to the 5 adhesive agent layer 2 on the both sides of the adhesive sheet 1 which project from the both ends of the ointment protect cover 7B, and the inner ends of the separable paper 8 extend to the undersurface of the both ends of the ointment protect cover 7B, so as to form overlapping ends 8a and 8a' by turning the extended portions thereof upwardly, and then the both ends of the ointment protect cover 7B are placed on the overlapping ends 8a and 8a'.

Since the first aid adhesive plaster as mentioned above, is in a state prior to use that the undersurface of the periphery of the blister 71B of the ointment protect cover 7B which covers the pad 4, is applied to the adhesive sheet 1, air does not go into the blister 71B. Further, since the projections 76, which is made to project downwardly from the central portion of the undersurface of the ceiling 74 of the blister 71B, is contacted with and received by the uppersurface of the pad, even if a pressure acts on the uppersurface of the blister 71B, the blister 71B does not bend or deform toward the pad 4, and therefore it may avoid such a situation that a part of the ointment 3 is adhered to the undersurface of the ceiling of the blister 71b. By the way, the manner of use of the adhesive plaster is the same as the above mentioned embodiment and therefore its description is omitted here.

What is claimed is:

1. A first aid adhesive plaster comprising;
   a pad having an upper surface on which an ointment is laid,
   an adhesive sheet having a rectangular shape; said pad being applied in a central portion of an upper surface of the adhesive sheet, and
   an ointment protect cover formed to be a blister having a dome section by making its central portion project upwardly to form a gentle arc, wherein the pad is covered with the blister by applying the ointment protect cover onto the adhesive sheet separably while leaving a gap between the ointment on the pad and an undersurface of the blister, and further comprising;
   a guard film applied onto the undersurface of the pad, said guard film being made to prevent permeation of the composition of the adhesive agent of the adhesive sheet into the pad, and
   a net covering from the upper surface of the pad to the undersurface of the guard film, both sides of said net being fixed to the both sides of the pad integrally by means of hot melt, wherein the ointment is applied from the upper surface of the net onto the pad through the mesh of the net so as to support the ointment by means of the mesh of the net.

2. A first aid adhesive plaster comprising;
   a pad having an upper surface on which an ointment is laid,
   an adhesive sheet having a rectangular shape; said pad being applied in a central portion of an upper surface of the adhesive sheet, and
   an ointment protect cover formed to be a blister having a rectangular form in plain view by making four walls thereof higher than the height of a width of the pad having the ointment, and also by making its central portion of the ointment protect cover project, wherein the pad is covered with the blister by applying the ointment protect cover onto the adhesive sheet separably, further comprising;
   a guard film applied onto the undersurface of the pad, said guard film being made to prevent permeation of the composition of the adhesive agent of the adhesive sheet, and
   a net covering from the upper surface of the pad to the undersurface of the guard film, both sides of said net being fixed to the both sides of the pad integrally by means of hot melt, wherein the ointment is applied from the uppersurface of the net onto the pad through the mesh of the net so as to support the ointment by means of the mesh of the net.

3. The first aid adhesive plaster as claimed in claim 2, wherein the pad comprises at least two layers.

* * * * *

UNITED STATES PATENT AND TRADEMARK OFFICE
CERTIFICATE OF CORRECTION

PATENT NO. : 6,617,486 B1  Page 1 of 1
DATED : September 9, 2003
INVENTOR(S) : Takaaki Murata It is certified that error appears in the above-identified patent and that said Letters Patent is hereby corrected as shown below:

<u>Title page,</u>
Item [73], Assignee, should read -- Aso Seiyaku Kabushiki Kaisha --.

Signed and Sealed this

Twenty-eighth Day of October, 2003

JAMES E. ROGAN
*Director of the United States Patent and Trademark Office*